(12) United States Patent
Baker, Jr.

(10) Patent No.: US 7,713,196 B2
(45) Date of Patent: May 11, 2010

(54) METHOD FOR EVALUATING SKIN HYDRATION AND FLUID COMPARTMENTALIZATION

(75) Inventor: Clark R. Baker, Jr., Newman, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 11/716,481

(22) Filed: Mar. 9, 2007

(65) Prior Publication Data

US 2008/0221407 A1 Sep. 11, 2008

(51) Int. Cl.
*A61B 5/00* (2006.01)
(52) U.S. Cl. .................. 600/309; 604/506; 604/505
(58) Field of Classification Search ............. 604/506, 604/19, 48, 500, 22, 4.01, 272, 505; 600/311, 600/346, 390
See application file for complete search history.

(56) References Cited

U.S. PATENT DOCUMENTS

| | | | |
|---|---|---|---|
| 4,306,612 A | 12/1981 | Baker et al. | |
| 4,651,934 A | 3/1987 | Bender et al. | |
| 4,681,395 A | 7/1987 | Lindsay et al. | |
| 4,703,175 A | 10/1987 | Salour et al. | |
| 4,709,413 A | 11/1987 | Forrest et al. | |
| 4,711,525 A | 12/1987 | Feth | |
| 4,793,708 A | 12/1988 | Bednarz | |
| 4,832,034 A * | 5/1989 | Pizziconi et al. | 600/366 |
| 4,924,870 A | 5/1990 | Wlodarczyk et al. | |
| 5,020,912 A | 6/1991 | Pavlath | |
| 5,079,845 A | 1/1992 | Childers | |
| 5,089,697 A | 2/1992 | Prohaska | |
| 5,118,931 A | 6/1992 | Udd et al. | |
| 5,148,303 A | 9/1992 | Biard | |
| 5,196,714 A | 3/1993 | Garcia, Jr. et al. | |
| 5,214,487 A | 5/1993 | Pavlath et al. | |
| 5,286,980 A | 2/1994 | Richert | |
| 5,300,769 A | 4/1994 | Dahlin et al. | |
| 5,354,825 A | 10/1994 | Klainer et al. | |
| 5,355,208 A | 10/1994 | Crawford et al. | |
| 5,374,821 A | 12/1994 | Muhs et al. | |

(Continued)

FOREIGN PATENT DOCUMENTS

DE 19606025 8/1997

(Continued)

OTHER PUBLICATIONS

Relationship between interstitial fluid volume and pressure (compliance) in hypothyroid rats Helge Wiig and Tjøstolv Lund, Am J Physiol Heart Circ Physiol 281:1085-1092, 2001.*

(Continued)

*Primary Examiner*—Kevin C Sirmons
*Assistant Examiner*—Michael J Anderson
(74) *Attorney, Agent, or Firm*—Fletcher Yoder

(57) ABSTRACT

There is provided a system and method for evaluating skin hydration and fluid compartmentalization. The system includes a microneedle array configured to extract fluid from an interstitial space and a pressure sensor configured to measure a pressure differential between the interstitial space and ambient pressure during extraction of the fluid. A processor coupled to the pressure sensor is configured to compute a hydration index based on the pressure differential. A display coupled to the processor is configured to display the hydration index.

14 Claims, 5 Drawing Sheets

U.S. PATENT DOCUMENTS

| | | |
|---|---|---|
| 5,401,954 A | 3/1995 | Richert |
| 5,480,723 A | 1/1996 | Klainer et al. |
| 5,486,921 A | 1/1996 | Priest |
| 5,505,841 A * | 4/1996 | Pirbazari et al. ............... 210/90 |
| 5,598,489 A | 1/1997 | Pavlath et al. |
| 5,698,848 A | 12/1997 | Belk |
| 5,700,897 A | 12/1997 | Klainer et al. |
| 5,777,737 A | 7/1998 | Priest |
| 5,780,847 A | 7/1998 | Dawson et al. |
| 5,854,678 A | 12/1998 | Liu et al. |
| 5,898,496 A | 4/1999 | Huang et al. |
| 5,949,930 A | 9/1999 | Cordova et al. |
| 5,973,783 A | 10/1999 | Goldner et al. |
| 5,991,026 A | 11/1999 | Kluth et al. |
| 6,152,059 A | 11/2000 | Del Raso |
| 6,197,257 B1 | 3/2001 | Raskas |
| 6,219,575 B1 | 4/2001 | Nemati |
| 6,256,533 B1 | 7/2001 | Yuzhakov et al. |
| 6,271,766 B1 | 8/2001 | Didden et al. |
| 6,312,612 B1 * | 11/2001 | Sherman et al. ................ 216/2 |
| 6,334,856 B1 | 1/2002 | Allen et al. |
| 6,379,324 B1 | 4/2002 | Gartstein et al. |
| 6,418,260 B1 | 7/2002 | Komachiya et al. |
| 6,451,240 B1 | 9/2002 | Sherman et al. |
| 6,503,231 B1 | 1/2003 | Prausnitz et al. |
| 6,535,753 B1 | 3/2003 | Raskas |
| 6,549,796 B2 | 4/2003 | Sohrab |
| 6,563,589 B1 | 5/2003 | Bennett et al. |
| 6,591,124 B2 | 7/2003 | Sherman et al. |
| 6,652,478 B1 | 11/2003 | Gartstein et al. |
| 6,663,820 B2 | 12/2003 | Arias et al. |
| 6,671,527 B2 | 12/2003 | Petersson et al. |
| 6,692,456 B1 * | 2/2004 | Eppstein et al. ............... 604/22 |
| 6,738,654 B2 | 5/2004 | Sohrab |
| 6,743,211 B1 | 6/2004 | Prausnitz et al. |
| 6,774,354 B2 | 8/2004 | Ames |
| 6,790,179 B2 | 9/2004 | Skover |
| 6,795,727 B2 * | 9/2004 | Giammarusti ................ 604/20 |
| 6,797,276 B1 * | 9/2004 | Glenn et al. ............. 424/278.1 |
| 6,804,008 B1 | 10/2004 | Morison et al. |
| 6,811,307 B2 | 11/2004 | Crowe et al. |
| 6,840,910 B2 | 1/2005 | Skover |
| 6,855,117 B2 | 2/2005 | Skover |
| 6,873,865 B2 | 3/2005 | Steuer et al. |
| 6,881,203 B2 * | 4/2005 | Delmore et al. ............. 604/272 |
| 6,904,301 B2 | 6/2005 | Raskas |
| 6,931,277 B1 | 8/2005 | Yuzhakov et al. |
| 6,961,598 B2 | 11/2005 | Diab |
| 7,004,928 B2 | 2/2006 | Aceti et al. |
| 7,009,707 B2 | 3/2006 | Beresford et al. |
| 7,042,572 B2 | 5/2006 | Lange et al. |
| 7,046,888 B2 | 5/2006 | Ye et al. |
| 7,277,741 B2 | 10/2007 | Debreczeny et al. |
| 7,283,242 B2 | 10/2007 | Thornton |
| 7,297,151 B2 * | 11/2007 | Boecker et al. ............. 606/181 |
| 7,343,186 B2 | 3/2008 | Lamego et al. |
| 2002/0045859 A1 * | 4/2002 | Gartstein et al. ............ 604/117 |
| 2002/0058863 A1 | 5/2002 | Petersson et al. |
| 2002/0111377 A1 * | 8/2002 | Stinchcomb ................ 514/468 |
| 2002/0133129 A1 | 9/2002 | Arias et al. |
| 2002/0138049 A1 * | 9/2002 | Allen et al. ................. 604/272 |
| 2002/0169411 A1 | 11/2002 | Sherman et al. |
| 2002/0177764 A1 | 11/2002 | Sohrab |
| 2003/0045837 A1 * | 3/2003 | Delmore et al. ............. 604/173 |
| 2003/0083558 A1 | 5/2003 | Skover |
| 2003/0120179 A1 | 6/2003 | Skover |
| 2003/0130569 A1 | 7/2003 | Raskas |
| 2003/0153900 A1 | 8/2003 | Aceti et al. |
| 2003/0158472 A1 | 8/2003 | Sohrab |
| 2003/0225360 A1 * | 12/2003 | Eppstein et al. ............... 604/19 |
| 2004/0009096 A1 * | 1/2004 | Wellman .................... 422/44 |
| 2004/0039269 A1 | 2/2004 | Ward et al. |
| 2004/0039343 A1 * | 2/2004 | Eppstein et al. ............. 604/200 |
| 2004/0054393 A1 * | 3/2004 | Stemme et al. .............. 607/149 |
| 2004/0106163 A1 | 6/2004 | Workman, Jr. et al. |
| 2004/0146611 A1 | 7/2004 | Arias et al. |
| 2004/0162473 A1 | 8/2004 | Sohrab |
| 2004/0260162 A1 | 12/2004 | Rohleder et al. |
| 2004/0267205 A1 * | 12/2004 | Stemme et al. ............. 604/173 |
| 2005/0010090 A1 * | 1/2005 | Acosta et al. ............... 600/316 |
| 2005/0123897 A1 * | 6/2005 | Cevc et al. ..................... 435/4 |
| 2005/0143713 A1 * | 6/2005 | Delmore et al. ............. 604/506 |
| 2005/0177046 A1 | 8/2005 | Mills |
| 2005/0181033 A1 * | 8/2005 | Dekker et al. ................ 424/449 |
| 2005/0209556 A1 * | 9/2005 | Tresco et al. ............. 604/93.01 |
| 2005/0209565 A1 | 9/2005 | Yuzhakov et al. |
| 2005/0267346 A1 | 12/2005 | Faber et al. |
| 2005/0283057 A1 | 12/2005 | Raskas |
| 2006/0015058 A1 * | 1/2006 | Kellogg et al. ................ 604/22 |
| 2006/0052680 A1 | 3/2006 | Diab et al. |
| 2006/0058593 A1 * | 3/2006 | Drinan et al. ............... 600/301 |
| 2006/0074282 A1 | 4/2006 | Ward et al. |
| 2006/0094945 A1 * | 5/2006 | Barman et al. ............. 600/347 |
| 2006/0094946 A1 * | 5/2006 | Kellogg et al. ............. 600/347 |
| 2006/0094985 A1 | 5/2006 | Aceti et al. |
| 2006/0100567 A1 * | 5/2006 | Marchitto et al. ............. 604/19 |
| 2006/0116563 A1 | 6/2006 | Asano et al. |
| 2006/0127964 A1 * | 6/2006 | Ford et al. .................... 435/14 |
| 2006/0129225 A1 * | 6/2006 | Kopia et al. ................ 623/1.13 |
| 2006/0264730 A1 | 11/2006 | Stivoric et al. ............. 600/390 |
| 2006/0264893 A1 * | 11/2006 | Sage et al. ................. 604/501 |
| 2007/0031283 A1 * | 2/2007 | Davis et al. .................. 422/58 |
| 2007/0031495 A1 * | 2/2007 | Eppstein et al. ............. 424/473 |
| 2007/0032707 A1 | 2/2007 | Coakley et al. |
| 2007/0032709 A1 | 2/2007 | Coakley et al. |
| 2007/0032710 A1 | 2/2007 | Raridan et al. |
| 2007/0032711 A1 | 2/2007 | Coakley et al. |
| 2007/0032712 A1 | 2/2007 | Raridan et al. |
| 2007/0032713 A1 | 2/2007 | Eghbal et al. |
| 2007/0032716 A1 | 2/2007 | Raridan et al. |
| 2007/0073122 A1 | 3/2007 | Hoarau |
| 2007/0073123 A1 | 3/2007 | Raridan, Jr. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0078309 A1 | 4/2007 | Matlock |
| 2007/0078311 A1 | 4/2007 | Al-Ali et al. |
| 2007/0100255 A1 * | 5/2007 | Boecker et al. ............. 600/583 |
| 2007/0118027 A1 * | 5/2007 | Baker et al. ................ 600/310 |
| 2007/0255205 A1 * | 11/2007 | Griss et al. ............... 604/93.01 |
| 2007/0260129 A1 | 11/2007 | Chin |
| 2007/0260130 A1 | 11/2007 | Chin |
| 2007/0260131 A1 | 11/2007 | Chin |
| 2007/0270672 A1 * | 11/2007 | Hayter ...................... 600/309 |
| 2007/0276318 A1 * | 11/2007 | Henley ....................... 604/20 |
| 2007/0282178 A1 | 12/2007 | Scholler et al. |
| 2007/0282183 A1 | 12/2007 | Scholler et al. |
| 2008/0004513 A1 | 1/2008 | Walker et al. |
| 2008/0058622 A1 | 3/2008 | Baker |
| 2008/0063696 A1 * | 3/2008 | Glenn et al. ................ 424/445 |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076995 A1 | 3/2008 | Hoarau |
| 2008/0076996 A1 | 3/2008 | Hoarau |
| 2008/0154104 A1 | 6/2008 | Lamego et al. |
| 2008/0198361 A1 | 8/2008 | Kaushal et al. |
| 2008/0208011 A1 | 8/2008 | Shuler |

FOREIGN PATENT DOCUMENTS

| | | |
|---|---|---|
| WO | WO 99/07277 | 2/1999 |

WO    WO 2004/044557 A2    5/2004

OTHER PUBLICATIONS

Klabunde, Richard E. PhD, "Cardiovascular Physiology Concepts," Updated Nov. 3, 2006. http//:cvphysiology.com/Arrhythmias/A007b.

Martanto, Wijaya et al. "Microinfusion Using Hollow Microneedles," *Pharmaceutical Research*, vol. 23, No. 1, Jan. 2006, Springer Science + Business Media, Inc.

Prentice, Paul et al. "Membrane Disruption by Optically Controlled Microbubble Cavitation," Nature Physics, pp. 107-110, vol. 1, Nov. 2005. Nature Publishing Group. www.nature.com/naturephysics.

Martanto, Wijaya et al. "Fluid Dynamics in Conically Tapered Microneedles," AIChE Journal, pp. 104-113, Jun. 2005, pp. 1599-1607, vol. 51, No. 6. www.interscience.wiley.com.

Wang, Ping PhD et al. "Minimally Invasive Extraction of Dermal Interstitial Fluid for Glucose Monitoring Using Microneedles," Diabetes Technology & Therapeutics, pp. 131-141, vol. 7, No. 1, 2005. School of Chemical and Biomolecular Engineering and Institute for Bioengineering and Bioscience, Georgia Institute of Technology, Atlanta, Georgia.

De Backer, Daniel, et al., "Microvascular Blood Flow Is Altered in Patients with Sepsis," American Journal of Respiratory and Critical Care Medicine, vol. 166, pp. 98-104, (2002), http://ajrccm.atsjournals.org/cgi/content/full/166/1/98, Last accessed Feb. 16, 2007.

George Tech Research News, "Microneedles: Report Describes Progress in Developing New Technology for Painless Drug and Vaccine Delivery," Nov. 17, 2003, http://gtresearchnews.gatech.edu/newsrelease/needlespnas.htm, Last accessed Jan. 19, 2007.

George Tech Research News, "Taking the 'Ouch' Out of Needles: Arrays of Micron-Scale "Microneedles" Offer New Technique for Drug Delivery", Jun. 22, 1998, http://gtresearchnews.gatech.edu/newsrelease/NEEDLES.html, Last accessed Jan. 19, 2007.

Lee, Sanghoon, et al., "Microfluidic valve with cored glass microneedle for microinjection," The Royal Society of Chemistry 2003, Lab Chip, 2003, vol. 3, pp. 164-167.

Prausnitz, Mark R., Microneedle Technology for Medical Applications, Abstract, 2 pages, Jun. 5, 2006, presented in Pleasanton, California.

* cited by examiner

METHOD FOR EVALUATING SKIN HYDRATION AND FLUID COMPARTMENTALIZATION

TECHNICAL FIELD

The present invention relates generally to determining physiological parameters and, more particularly, to determining tissue hydration.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In healthy individuals, homeostatic control mechanisms ensure that a balance between fluid gain and fluid loss is maintained. Therefore, maintaining fluid balance is typically not an issue requiring attention. In ill individuals, however, the maintenance of body fluid balance may be cause for great concern. Dehydration or edema may occur if fluid balance is not properly maintained. For example, dehydration of infants and children suffering from diarrhea and/or vomiting can be life threatening if not recognized and treated promptly. Additionally, many elderly people have thin, fragile skin and, because skin is a major reservoir of water for the body, have an increased risk of dehydration.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention a method for determining skin hydration is provided. The method includes extracting fluid through microneedles inserted into skin and determining the pressure gradient required to extract the fluid. The pressure gradient is then correlated to a hydration index.

In accordance with another aspect of the present invention a method to determine if leakage from a vascular compartment is occurring is provided. The method includes extracting fluid from an interstitial space using a microneedle array and spectroscopically analyzing the extracted fluid to determine if blood or inflammation specific analytes are present in the interstitial fluid.

In accordance with yet another aspect of the present invention a system for evaluating skin hydration is provided. The system includes a microneedle array configured to extract fluid from an interstitial space and a pressure sensor configured to measure a pressure differential between the interstitial space and ambient pressure during the extraction of the fluid. A processor is coupled to the pressure sensor and configured to compute an interstitial volume based on the pressure differential and a display is coupled to the processor and configured to display the interstitial volume.

BRIEF DESCRIPTION OF THE DRAWINGS

Certain exemplary embodiments are described in the following detailed description and in reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, a system and methods are disclosed for evaluating skin hydration and fluid compartmentalization. The technique includes using microneedles to extract and analyze interstitial fluid. As described in detail below, the technique may include using a pressure gradient (positive or negative) required to extract the fluid to determine an index of local skin hydration and/or systemic hydration. In one embodiment, the pressure gradient may be used in combination with skin thickness to determine the hydration index. The technique may also include measuring blood or inflammation-specific analyte concentrations to determine if leakage from a vascular compartment is occurring. Additionally, the technique may include measuring the cell-specific analyte concentrations to assess the contribution of intracellular fluid or to quantify the extent of cellular trauma in response to the insertion of microneedles.

Figure 1:
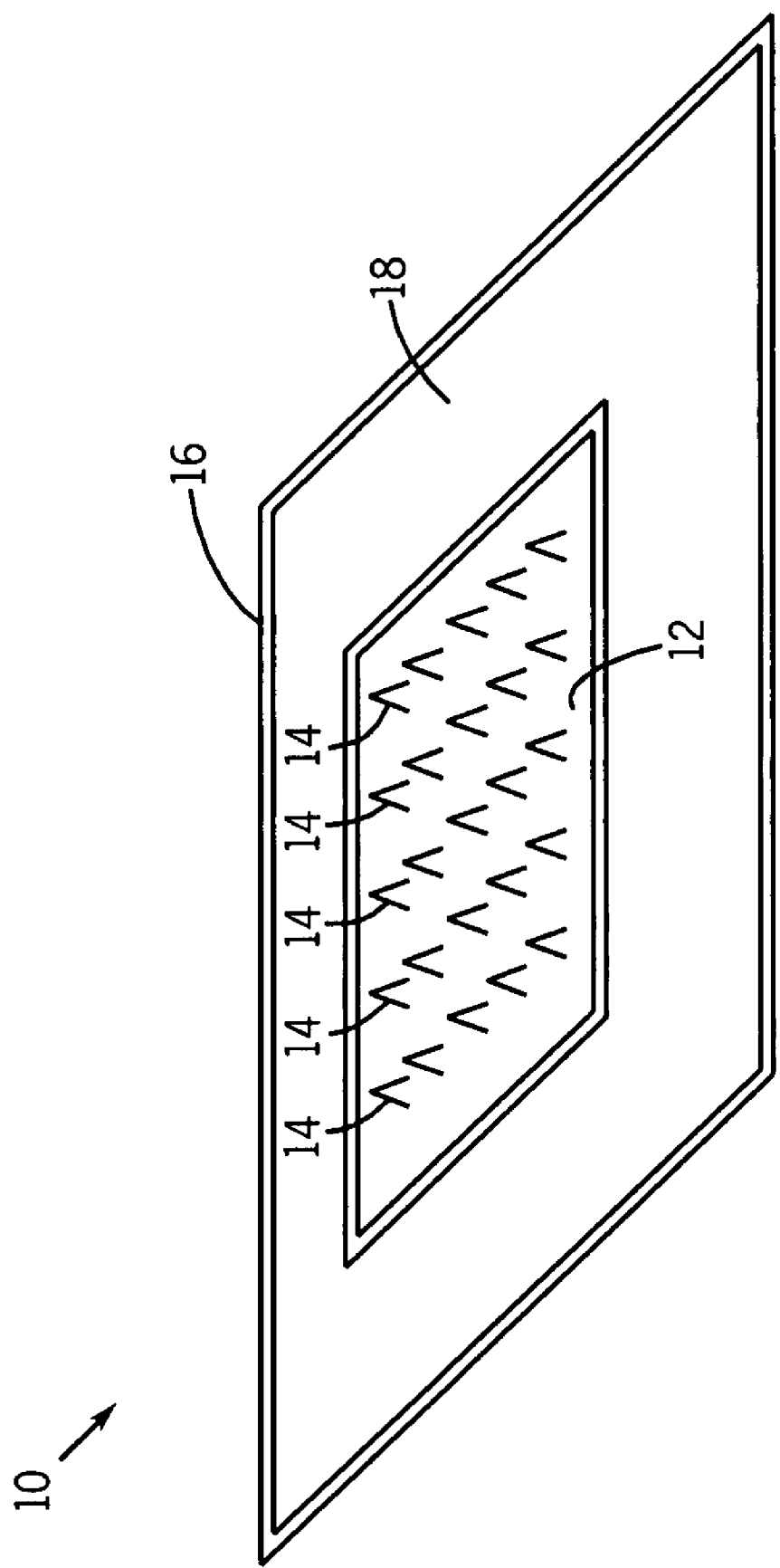
FIG. 1 illustrates a microneedle array unit in accordance with an exemplary embodiment of the present invention.

Turning to FIG. 1, a microneedle array unit is shown in accordance with an exemplary embodiment of the present invention and generally referred to by the reference numeral 10. As its name suggests, the microneedle array unit 10 has a microneedle array 12 which is an arrangement of a plurality of micron-scaled needles 14. The microneedle array 12 may be created using microfabrication techniques known in the art. For example, the microneedle array 12 may be manufactured using photolithography and plasma etching of silicon wafers, electrodepositing metal onto laser drilled polymeric molds, or beveling blunt-tip microneedles formed by pulling fire-polished boro-silicate glass pipettes. Currently, microneedle arrays are not available commercially, but multiple companies are working to make them manufacturable and have prototypes available.

The microneedle array unit 10 may also include backing material 16 and an adhesive area 18. The backing material 16 may be configured to be removed to allow for the sampling of interstitial fluid, as will be discussed in detail below. The adhesive area 18 allows for the microneedle array 12 to remain in place during sampling of the interstitial fluid.

Figure 2:
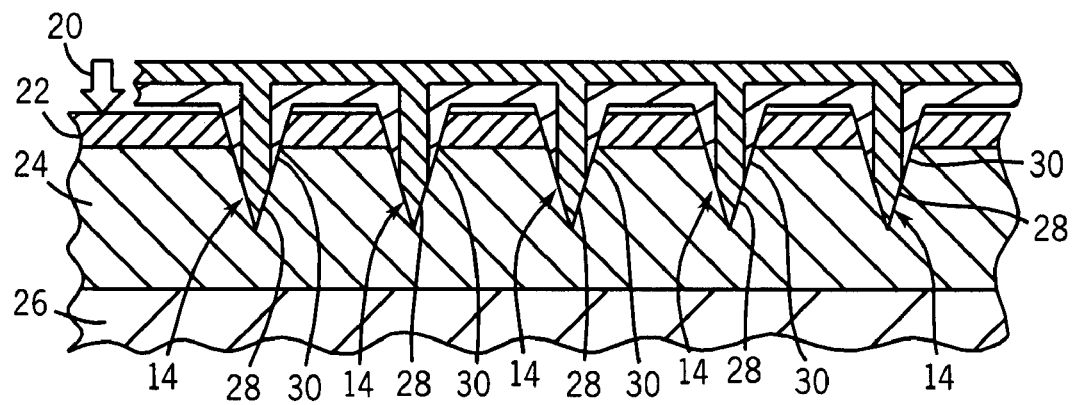
FIG. 2 illustrates a cross-sectional view of a microneedle array being inserted into the skin of a patient in accordance with an exemplary embodiment of the present invention.

A cross-sectional view of the micro-scaled needles 14 being inserted into the skin of a patient is shown in FIG. 2 and indicated by arrow 20. As can be seen, the micro-scaled needles 14 penetrate through an epidermis layer 22 into a dermis layer 24. The micro-scaled needles 14 do not typically penetrate deep enough to reach an underlying capillary bed 26, so blood is not typically sampled through the micro-scaled needles. The micron scaled needles may be longer for thick-skinned adults and shorter for elderly, neonatal and infants, since their skin is thinner. Accordingly, the micro-scaled needles 14 may be between 150 to 250 microns long, although in alternative embodiments the needles may have lengths greater than 250 microns. The diameter of the micro-scaled needles 14 may be from tens of microns down to 0.2 microns, for example. Because of their small size, the micro-scaled needles 14 are able to sample interstitial fluid (ISF) from the interstitial space, penetrating the skin with minimal sensation, without compromising the skin's function as protective barrier and without puncturing the vasculature.

The micro-scaled needles 14 may be configured as single needles or, alternatively, as illustrated in FIG. 2, two-needle units. If the micro-scaled needles 14 are configured as single needles, each microneedle 14 will have a hollow interior through which the fluid is able to flow. Additionally, the single needle unit may have a beveled, tapered point to allow for easy insertion into the skin. The two-needle units may include inner needles 28 positioned within outer needles 30. The inner needles 28 are solid needles with a sharp point for puncturing the skin, while the outer needles 30 are hollow and configured to sample fluid, as will be discussed in greater detail below. Additionally, the outer needles 30 may be made of a polymer containing anti-clotting agents, such as EDTA or heparin, to prevent the sampled fluid from clotting.

Figure 3:
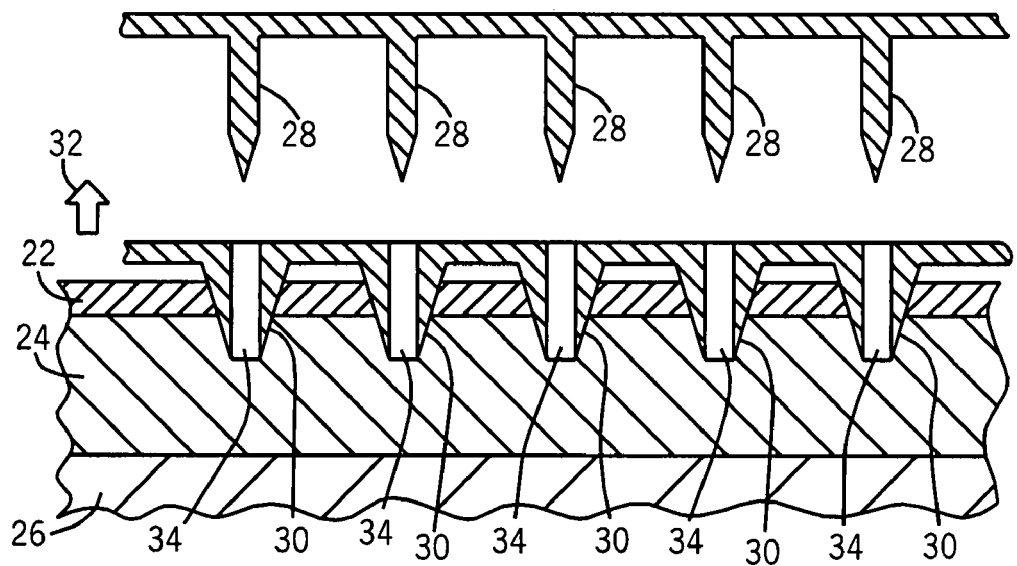
FIG. 3 illustrates the removal of inner needles from the microneedle array in accordance with an exemplary embodiment of the present invention.

After the two-needle micro-scaled needles 14 have been inserted into the skin, the inner needles 28 may be removed from microneedle array 12 as indicated by arrows 32 in FIG. 3. As mentioned above, this may entail removal of the backing material 16 to which the inner needles 28 may be coupled. The removal of the inner needles 28 vacates an aperture 34 of the outer needles 30 through which fluid from the interstitial space of the dermis 24 may flow. Additionally, the removal of the inner needles 28 exposes a top surface 36 of the outer needles 30.

Figure 4:
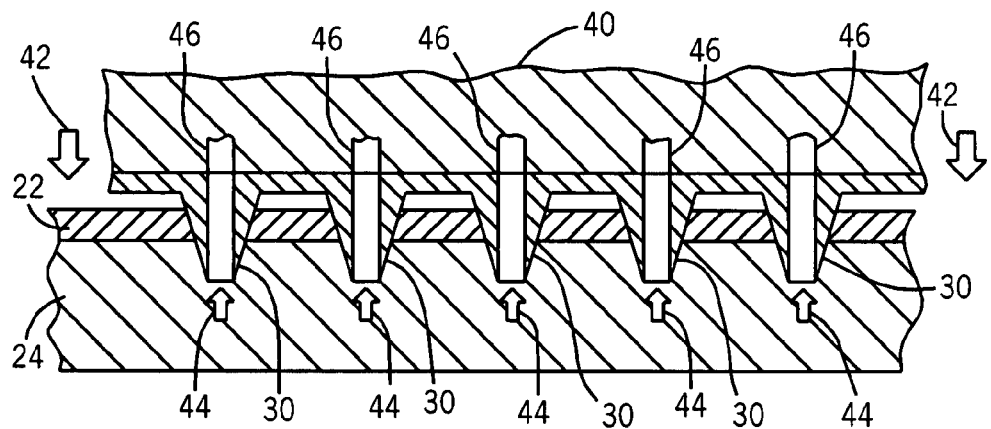
FIG. 4 illustrates attachment of a sampling piece to the outer needles of the microneedle array of FIG. 2 in accordance with an exemplary embodiment of the present invention.

A sampling piece 40, shown in FIG. 4, can be coupled to the exposed top surface 36, as indicated by arrows 42. The sampling piece 40 can be used to collect the fluid extracted from the interstitial space via the outer needles 30. As indicated by arrows 44, fluid may flow from the interstitial space into the apertures 34 of the outer needles 30. The sampling piece 40 is configured to receive the fluid extracted from the interstitial space through apertures 46 which are aligned with apertures 34 of the outer needles 30.

Figure 5:
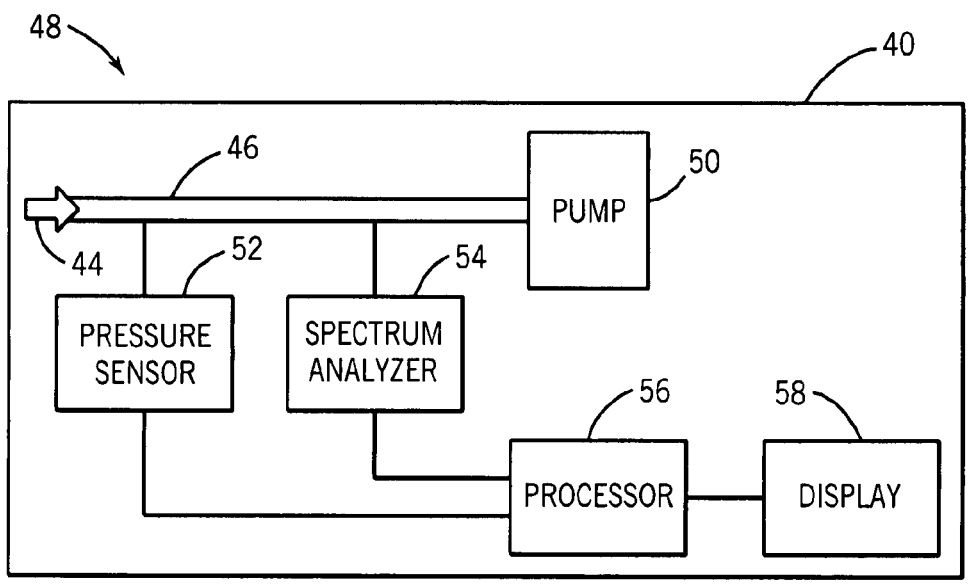
FIG. 5 illustrates a block diagram of the sampling piece of FIG. 4 in accordance with an exemplary embodiment of the present invention.

A block diagram of the sampling piece 40 is illustrated in FIG. 5. The sampling piece 40 may include a pump 50, a pressure sensor 52, a spectrum analyzer 54, a processor 56, and a display 58. The pump 50 may be any type of pump suitable for use in the extraction of small amounts of fluid via the microneedle array 12. For example, the pump may be a piezoelectric pump or a syringe pump. Alternatively, the pump may be configured to pneumatically operate a valve to control the flow of fluid. The pump 50 is coupled to the aperture 46 and may aid in the extraction of fluid from the interstitial space of the dermis layer 24. Specifically, the pump 50 may provide positive or negative pressure to control the flow of interstitial fluid into the sampling piece 40.

The pressure sensor 52 may be any suitable pressure sensor capable of determining a pressure gradient between the interstitial fluid and the ambient pressure and/or determining the amount of pressure required to withdraw fluid from the interstitial space. For example, in accordance with an exemplary embodiment, the pressure sensor 52 may be a fiber-optic pressure sensor configured to measure interference changes in light that reflects from a deformable membrane. The deformable membrane may be made with a polyurethane material. The fiber optic pressure sensor may be capable of measuring pressures in the range of 0-40 kPa with a resolution of 10 Pa (1 Pa=0.0075 mmHg). Additionally, the fiber optic pressure sensor may be produced on a micro scale, i.e., with a 125 micron diameter, so that it is sufficiently small to mate with the microneedles. In an alternative exemplary embodiment, and on an even smaller scale, the fiber optic pressure sensor may use a silicon diaphragm and a corresponding pressure cavity that is as small as 0.050 microns in diameter, as disclosed in U.S. Pat. No. 6,925,213.

Regardless of the particular type of pressure sensor implemented, the pressure sensor 52 is configured to determine whether a negative or positive pressure is required to withdraw the interstitial fluid using the microneedle array 12, as mentioned above. The pressure sensor 52 is communicatively coupled with the processor 56 and is configured to indicate to the processor 56 the positive or negative pressure gradient and/or the amount of pressure required to withdraw fluid from the interstitial space. Upon receiving the pressure information, the processor 56 may correlate it with a hydration index indicative of a local hydration level or a systemic hydration level, and/or the volume of the interstitial space.

Figure 6:
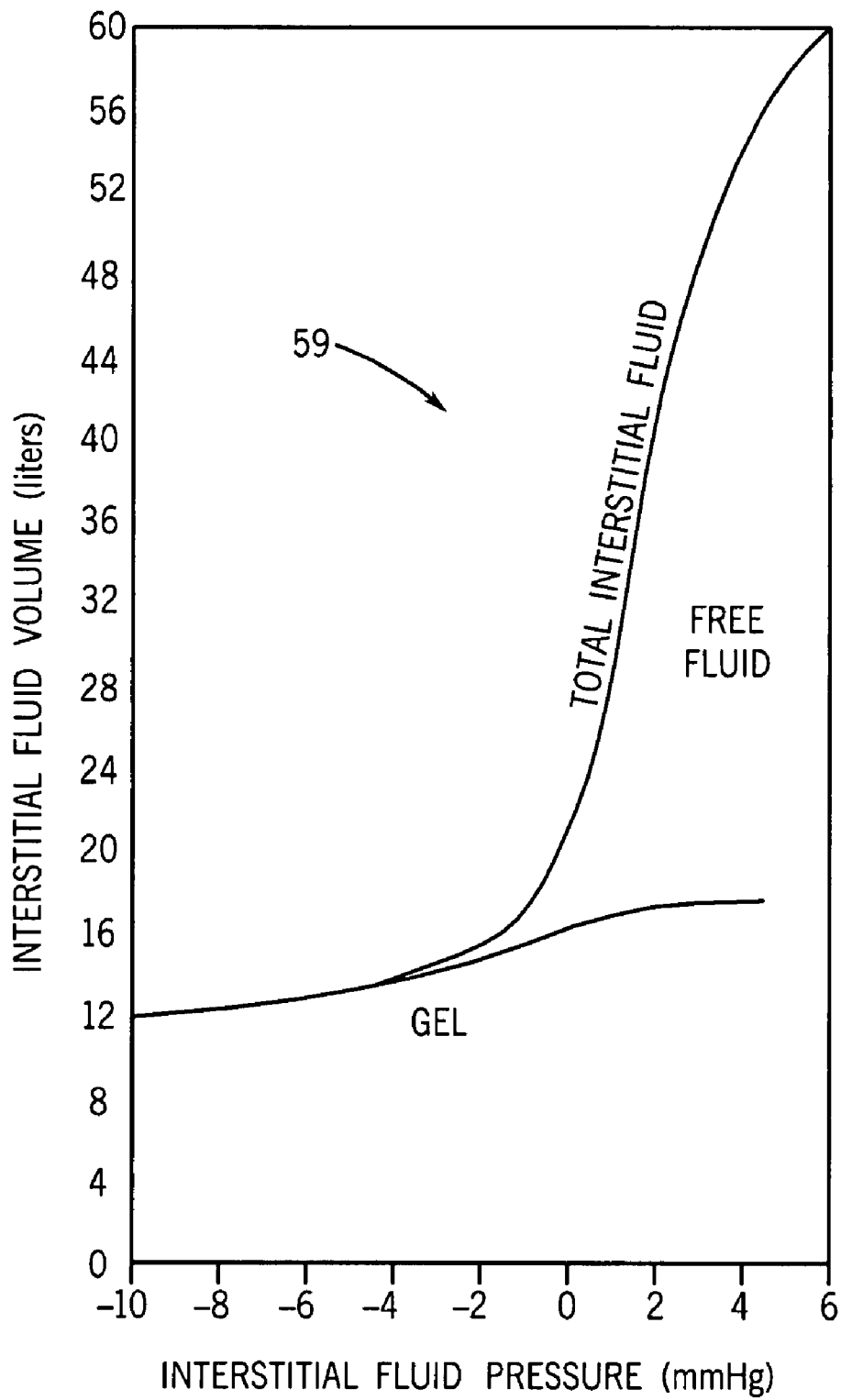
FIG. 6 illustrates a plot of the interstitial fluid pressure and the interstitial fluid volume.

Referring to FIG. 6, the relationship between the interstitial fluid pressure and the interstitial fluid volume is illustrated as a plot 59. The interstitial fluid pressure in millimeters of mercury (mm Hg) is the x-axis and the interstitial fluid volume in liters is on the y-axis. The total interstitial fluid is shown as having two parts, a gel and a free fluid. The fluid in the gel is bound to extracellular matrix proteins and not able to move around the body. Additionally, the volume of the gel is relatively constant across a range of pressures. As can be seen in the plot 59, when there is negative pressure, i.e., less than zero pressure, in the interstitial cavity, most of the fluid in the interstitial compartment is found in the gel. However, relatively small increases in pressure result in large increases of volume when there is positive pressure. Accordingly, it is the free fluid volume that is most affected by interstitial pressure changes, so it is primarily the free fluid that is extracted through the microneedle array 12. The hydration index, therefore, may be derived by correlating the measured pressure required to extract interstitial fluid with the volume of free fluid according to the plot 59.

The intracellular fluid in euhydrated humans has a slightly negative pressure relative to ambient. As such, if the pressure sensor indicates that the interstitial fluid has a positive pressure differential relative to ambient, it may indicate that inflammation is occurring or fluid is leaking into the measured compartment. Additionally, because it is known that the intercellular fluid pressure increase with interstitial volume, the pressure measurement may also be translated into a compartmental volume measurement when adjusted for skin thickness, as thicker skin should have a greater capacity for storing interstitial fluid at any given interstitial pressure.

Skin thickness may be determined in a number of ways known in the art. For example, the skin thickness may be determined using ultrasound or caliper measurements. Alternatively, the skin thickness may be determined spectroscopically as described in U.S. patent Ser. No. 11/716,778, entitled "Method and Apparatus for Estimating Water Reserves," which is incorporated herein by reference. The skin thickness measurement and the pressure measurement may be combined to determine the volume of the compartment.

The characterization of the relationship between the pressure in the interstitial space and the presence or absence of flow at a given pressure gradient may depend on the resistance of the aperture 34 of the micro-scaled needles 14. Therefore, a calibration factor may be used to compensate for the resistance. The calibration factor may be determined based on empirical testing of the microneedle array 12 to determine the relationship between the flow rate and a pressure drop along across the microneedle array 12. Specifically, the testing may include supplying a series of known pressures to the microneedle array 12 and measuring the resultant flow of a fluid, such a saline solution, for example. Alternatively, the calibration may include measuring an amount of pressure required to maintain known flow rates through the microneedles.

Returning to FIG. 5, the extracted interstitial fluid may be analyzed spectroscopically and/or chemically to determine if there is leakage from a vascular compartment or to determine the extent of trauma caused by insertion of the micro-scaled needles 14 into the skin. The interstitial fluid typically comprises about 75% of extracellular fluid in the human body and the compartmentalization of fluids may be determined by measuring the concentration of specific analytes in the interstitial fluid withdrawn through the microneedle array 12. Specifically, the presence and concentration of specific proteins, such as albumin or cytokines may indicate that the microvasculature is becoming leaky or that an inflammatory process is occurring.

The compartmentalization of extracellular fluid between the vascular and interstitial space is maintained by oncotic pressure supplied by proteins in blood plasma and the fenestrae between the vascular endothelial cells. Albumin is the most prominent protein in the blood plasma and its presence and concentration can be determined by the processor 56 using the spectral information gathered by the spectrum analyzer 54. For example, near-infrared spectroscopy techniques common and known in the art may be employed which determine the relative concentration of albumin or other proteins and water.

The spectrum analyzer 54 may be integrated with the sampling piece 40, as illustrated in FIG. 5 or, alternatively, it may be independent of the sampling piece 40. For example, small spectrum analyzers, such as micro-electro-mechanical system (MEMS) and solid state micro spectrometers, may be integrated into the sampling piece 40 without significantly increasing the size and weight of the sampling piece 40. Alternatively, fiber optics may be coupled to the sampling piece to allow for an independent spectrometer to perform the spectral analysis.

Figure 7:
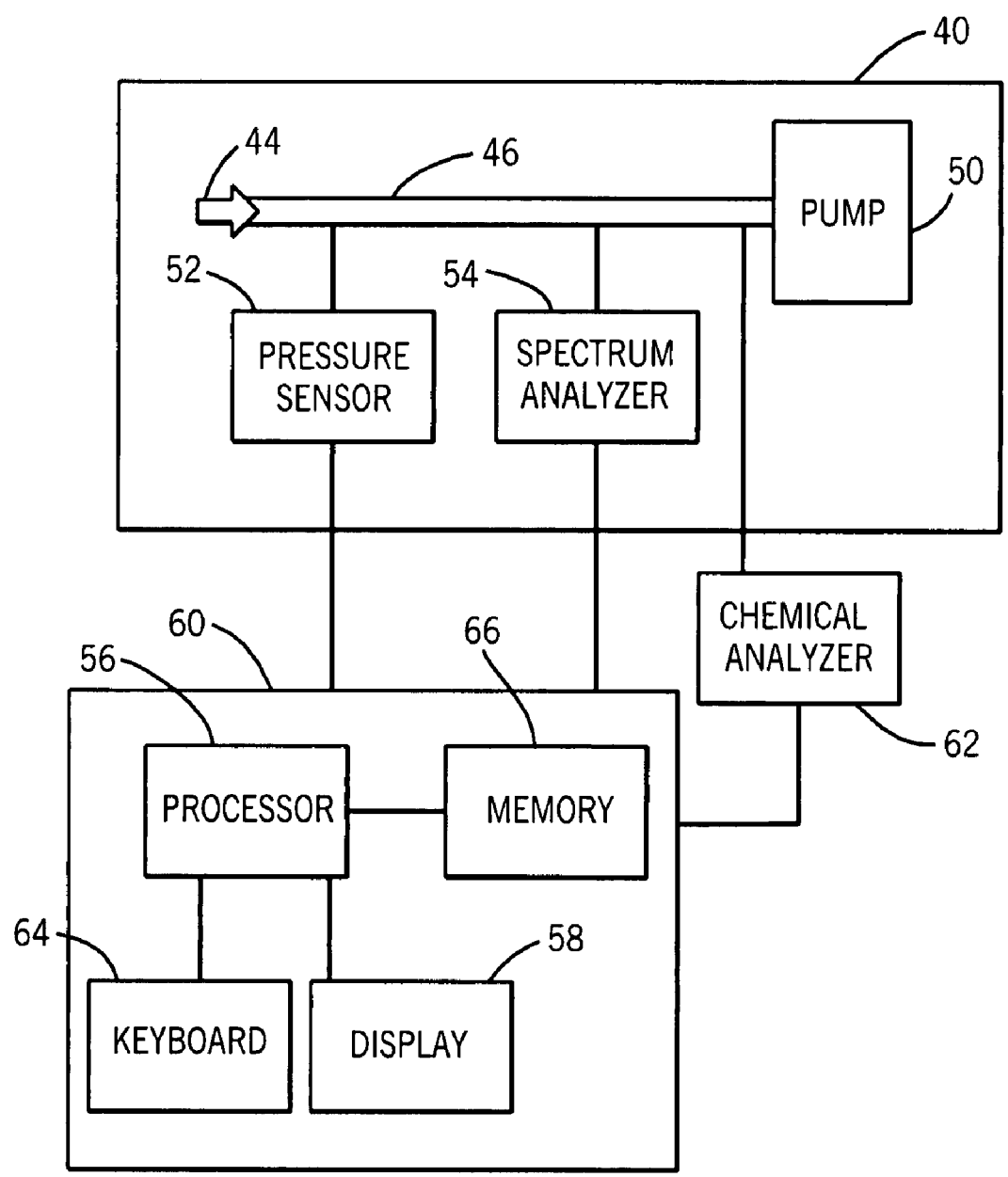
FIG. 7 illustrates a block diagram of the sampling piece coupled with a chemical analyzer and a monitor in accordance with an alternative exemplary embodiment of the present invention.

Turning to FIG. 7, an alternative embodiment of the sampling piece 40 is illustrated, wherein the processor 56 and display 58 are located in a monitor 60 and a chemical analyzer 62 is provided. The chemical analyzer 62 may be configured to receive the sampled fluid directly from the sampling piece 40 or, alternatively, the sampled fluid may be manually extracted from the sampling piece 40 for chemical analysis by the chemical analyzer 62. The chemical analyzer 62 may perform tests to determine the chemical make-up of the sampled fluid, as discussed below. Additionally, because space constraints of the sampling piece 40 are no longer a factor, additional features, such as a keyboard 64, may be provided to allow a user to enter information, such as skin thickness, for example, into the monitor 60.

Cell membranes in the interstitial space have K—Na-ATPase pumps to keep sodium ($Na^+$) in the extracellular spaces and potassium ($K^+$) in the intracellular space. Normal concentrations of extracellular sodium and intracellular potassium are respectively 139 mmol and 140 milliOsmoles/liter. The K—Na-ATPase pumps effectively enforce the compartmentalization of water in the body so that most changes in fluid volume are primarily extracellular, including changes due to an intravenous fluid administration. During the sampling of the interstitial fluid, some micro-scaled needles 14 in the microneedle array 12 may pierce cells so that the sampled fluid includes intracellular fluid. The combination of intracellular and interstitial fluids adds heterogeneity to the composition of the sampled fluid and may cause constituents of the extracted interstitial fluid to be diluted.

The effects of intracellular fluid contaminations on predominantly interstitial fluid analysis may be discounted by determining the potassium concentration using a chemical analyzer 62. Specifically, the potassium concentration measurement may be used in making an adjustment proportional to the mean potassium concentration in the sampled fluids. For example, if the potassium concentration was 10% of the sodium concentration, and the extracted fluid contained 0.09% albumin, the estimate of albumin concentration in extracellular fluid may be adjusted upward to 0.10%. Alternatively, the sampled fluid can be analyzed using the chemical analyzer 62 on a per micro-scaled needle 12 or per group of micro-scaled needles basis to determine if the sampled fluid exceeds a threshold level for potassium concentration. If it is determined that the fluid from specific needles exceeds the threshold, then fluids from those micro-scaled needles 14 can be excluded from the interstitial fluid analysis.

Additionally, the amount of extracted fluid which can be attributed to intracellular sources may be indicative of the relative strength of the cell membranes. Specifically, the degree to which the microneedle array 12 pierces cells, as indicated by specific intracellular analytes, such as potassium, may provide an indication of the integrity and strength of cell membranes.

The results of the pressure sensor 52, spectrum analyzer 54, and/or chemical analyzer 62 may be provided the processor 56, as discussed above, for further processing and interpretation of the information. The processor may output information via the display 58. Depending on the sophistication of the monitor 60 and display 58, the display may be configured to indicate interstitial pressure, interstitial volume, skin hydration level, fluid compartmentalization values, cell strength, cell trauma resulting from insertion of the microneedle array 12, etc.

Additionally, in yet another alternative embodiment, the processor 56 may be configured to use the information gathered through the aforementioned analysis, including interstitial fluid pressure, interstitial fluid volume, fluid constituent analysis and vasculature leakiness determination, in conjunction with a blood pressure measurement, which may be provided automatically or manually, to regulate the administration and selection of fluid resuscitation. For example, a system might deliver colloid solutions to a hypotensive patient with above average interstitial fluid pressure and little or not interstitial protein. Alternatively, the system may deliver crystalloid solutions to a hypotensive patient having low-to-normal interstitial fluid pressure or interstitial proteins indicative of leaky vasculature, with a goal of maintaining desired hydration and blood pressure targets.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of tissue hydration, but these techniques may also be utilized for the measurement and/or analysis of other analytes. The invention, therefore, is to cover all modifications, equivalents, and alternatives falling within the spirit and scope of the invention as defined by the following appended claims.

What is claimed is:

1. A method for determining hydration comprising:
   extracting fluid through microneedles inserted into skin;
   determining the pressure gradient required to extract the fluid; and
   determining a hydration index based on the pressure gradient.

2. The method of claim 1, wherein the hydration index is representative of the hydration of the skin.

3. The method of claim 1, wherein the hydration index is representative of the hydration of the body.

4. The method of claim 1 comprising combining a skin thickness value with the pressure gradient to determine the volume of a compartment of the skin.

5. The method of claim 1 comprising measuring blood specific analytes in the fluid to determine leakage from a vascular compartment.

6. The method of claim 5 wherein the blood specific analytes comprise albumin or other plasma proteins.

7. The method of claim 1 comprising measuring inflammation-specific analyte concentration.

8. The method of claim 1 comprising measuring intracellular-specific analyte concentrations to assess the contribution of intercellular fluid.

9. The method of claim 8 wherein the measuring intracellular-specific analyte concentration comprises measuring potassium concentration.

10. The method of claim 8 comprising quantifying the extent of cellular trauma in response to insertion of microneedles based on the contribution of intercellular fluid.

11. The method of claim 1, wherein determining the hydration index based on the pressure gradient comprises determining whether the fluid has a positive pressure differential relative to ambient pressure.

12. The method of claim 1, wherein determining the pressure gradient required to extract the fluid comprises measuring the amount of pressure required to extract the interstitial fluid.

13. The method of claim 12, wherein determining the hydration index comprises correlating the measured pressure required to extract the interstitial fluid with a volume of free fluid in an interstitial space.

14. The method of claim 1, wherein determining the pressure gradient required to extract the fluid comprises using a calibration factor to compensate for resistance of fluid flow caused by the microneedles.

* * * * *